United States Patent [19]
Bombardelli et al.

[11] Patent Number: 5,897,866
[45] Date of Patent: Apr. 27, 1999

[54] PROCESS FOR THE EXTRACTION OF LYCOPENE USING PHOSPHOLIPID IN THE EXTRACTION MEDIUM

[75] Inventors: Ezio Bombardelli; Paolo Morazzoni; Roberto Seghizzi, all of Milan, Italy

[73] Assignee: Indena S.p.A., Milan, Italy

[21] Appl. No.: 08/890,165

[22] Filed: Jul. 9, 1997

[30] Foreign Application Priority Data

Jul. 12, 1996 [IT] Italy .................................. MI96A1442

[51] Int. Cl.⁶ .................................................. A01N 65/00
[52] U.S. Cl. ...................... 424/195.1; 426/425; 426/429; 426/478; 514/762
[58] Field of Search .................. 424/195.1; 426/425, 426/429, 478; 514/762

[56] References Cited

U.S. PATENT DOCUMENTS

| | | | |
|---|---|---|---|
| 3,081,171 | 3/1963 | Reiners et al. | 99/2 |
| 4,851,339 | 7/1989 | Hills | 435/67 |
| 4,996,069 | 2/1991 | De Hey et al. | 426/248 |
| 5,035,909 | 7/1991 | Lomelin et al. | 426/473 |
| 5,180,747 | 1/1993 | Matsuda et al. | 514/681 |

FOREIGN PATENT DOCUMENTS

| | | |
|---|---|---|
| 0 600 544 | 6/1994 | European Pat. Off. . |
| 0 659 402 | 6/1995 | European Pat. Off. . |
| 56-08459 | 1/1981 | Japan . |
| 2280110 | 1/1995 | United Kingdom . |
| WO 9516363 | 6/1995 | WIPO . |

OTHER PUBLICATIONS

Japanese Patent Abstract, Section Ch, Week 9418, Derwent Publications Ltd., London, GB; Class B07, AN 94–148154 JP 06 093 285 A (Hasegawa Co Ltd), Apr. 5, 1994.

Japanese Patent Abstract, Section Ch, Week 9532, Derwent Publications Ltd., London, GB; Class D13, AN 95–242717, JP 07 147 929 A, Kagome KK, Jun. 13, 1995.

*Primary Examiner*—Sandra E. Saucier
*Attorney, Agent, or Firm*—Pennie & Edmonds LLP

[57] ABSTRACT

The present invention relates to a process for the preparation of pure lycopene or of lipophilic extracts containing it from whole fruits of *Lycopersicum esculentum* and similar species or parts thereof obtainable as by-products of food industry processes. The partially dehydrated fresh material is extracted with aliphatic or aromatic hydrocarbons or water-immiscible solvents in the presence of phospholipids as surfactant and stabilizing agents and the extracts are concentrated to an oil or fractionated to the desired lycopene concentration.

22 Claims, No Drawings

PROCESS FOR THE EXTRACTION OF LYCOPENE USING PHOSPHOLIPID IN THE EXTRACTION MEDIUM

TECHNICAL FIELD

The present invention relates to a process for the extraction of lycopene.

BACKGROUND OF THE INVENTION

Lycopene is a highly lipophilic procarotenoid present in greatest amounts in the species Lycopersicum although it may be found in lower amounts in other vegetable and algae species. Lycopene is present in common tomatoes in concentrations ranging from 30 to 100 ppm, on the average at 50 ppm. It is usually present as a secondary metabolite in mammals, where it plays an important role as an antioxidant and free-radicals scavenger, together with substances such as Vitamin E, Vitamin C and other compounds. At the plasma level, lycopene has been found to be incorporated in low-density lipoproteins in which it decreases the oxidation of cholesterol and of other lipids, thus preventing vascular damage. Moreover, an inverse correlation between lycopene blood levels and prostate tumor has recently been proved. The administration of lycopene to humans is therefore important in reducing the risk of tumors and atherosclerosis; hence the need for stable formulations containing lycopene for a preventive chronic treatment in humans.

SUMMARY OF THE INVENTION

The invention relates to a process for extracting lycopene from *Lycopersicum esculentum* by combining a quantity of *Lycopersicum esculentum* containing lycopene with an extraction medium comprising at least one solvent chosen from aromatic hydrocarbons, aliphatic hydrocarbons and halohydrocarbons and from about 0.01 to about 0.100 w/v of a phospholipid. A sufficient amount of the extraction medium may be added to remove all or a portion, as desired, of the lycopene from the *Lycopersicum esculentum*. The preferred solvents are n-hexane and methylene chloride, most preferably n-hexane. The preferred phospholipid is soy lecithin.

Prior to the extraction step the *Lycopersicum esculentum* may be formed into a slurry by at least partially homogenizing the material, e.g., with a knife mill. The slurry may then be heated to a temperature of from about 70–100° C. for between about 15–60 minutes and then cooled at a temperature of between about 50–70° C. This cooling step is preferably carried out under sterile conditions. In one embodiment of the invention the starting plant material is at least partially dried and the method further comprises adding to the slurry about one-half part by weight of water to lyse the cells of the *Lycopersicum esculentum*, thus facilitating release of the lycopene.

The *Lycopersicum esculentum* may be extracted one or a plurality of times in order to obtain the lycopene contained therein. The resultant extract(s) may be individually or collectively concentrated by removing a portion of the extraction medium. In a preferred embodiment the extract is concentrated such that the lycopene is present in an amount of from about 1 to about 10% by weight.

The lycopene extract, whether concentrated or not, may, if desired, be further purified. In one embodiment the purification is carried out by chromatographic separation through an acidic alumina column wherein the lycopene is eluted with a mixture of ethyl acetate and hexane. Alternatively, the purification may be obtained by extraction with carbon dioxide ($CO_2$) under supercritical conditions, i.e., at a temperature of between about 35–60° C. and at a pressure of between about 150–200 bars.

In a further embodiment, the lycopene extract thus obtained can be added to, e.g., food and cosmetic compositions suitable for use by humans.

DETAILED DESCRIPTION OF THE INVENTION

According to the invention, fruits of Lycopersicum sp. are homogenized, e.g., with a knife mill and the resulting semi-liquid mass is heated to temperatures varying from 70 to 100° C., preferably at 90° C., for a time from 15 to 60 minutes, preferably for about 30 minutes. During heating, an abundant precipitate forms, which includes substantially all of the lycopene present in the biomass. The suspension is cooled at preferably 60° C., keeping the medium sterile, then centrigued through fast decanters or filtered through pressure-filters.

The centrifugation or filtration residue, containing about 20% of residual water, can immediately be extracted with stirring or continuously with, for example, hydrocarbons, or it can be frozen to preserve it until the extraction. The residue when immediately extracted, is suspended in a sufficient amount, preferably about 10 vol., of the selected solvent, preferably n-hexane, containing, e.g., soy lecithin at concentrations varying from 0.01 to 0.1%, preferably 0.02%, according to the procedure reported below in the examples. The solvents used in these conditions extract lycopene which generally goes into solution in the first extraction, in a highly selective way, leaving other carotenoids, such as beta-carotene, in the biomass. The extracts are concentrated until the solvent is completely removed, thereby obtaining oily residues containing up to 10% of lycopene.

An economically interesting source for the preparation of lycopene are the by-products of the preserved food industry, such as the skins of mature fruits and those fibrous portions which are not green. These materials can be quickly dried or, more preferably, frozen, optionally after removing seeds which are usually present. When the vegetable material is frozen before extraction, the biomass must be ground at temperatures ranging from −25 to −10° C., preferably below −15° C. so as to homogenize it. Subsequently the residue is extracted according to the procedures described herein for use with the whole fruits. If the vegetable material is dried before the extraction it is finely ground and treated with about one-half its weight of water to cause the cells to lyse, thus promoting the extraction. The humid vegetable material is then extracted with aliphatic hydrocarbons or other solvents as described above for the whole fruits. Suitable amounts of phospholipids are added to assist the extraction and avoid lycopene oxidative degradation. These biomasses yield, after evaporation of the extraction solvent, lipid extracts containing one to ten percent of lycopene. Pure lycopene can be prepared from these extracts by chromatography using acidic alumina columns and eluting the product with ethyl acetate/hexane mixtures with a variable gradient. Alternatively, lycopene can be prepared by extracting the lipophilic extract resulting from the concentration of the extraction solvents by partitioning the concentrate with $CO_2$ under supercritical conditions with multistep columns in a manner well known in the art. For example, lycopene can be purified using a three-step partitioning column, keeping the pressure constant in a range from 150 to 200 bars, preferably under 180 bars and a segment temperature ranging from 35 to 65° C. In these supercritical conditions a substantial purification of the extract and the recovery of lycopene by crystallization of the residue undistilled during fractionation can be obtained. The products obtained according to the invention can be incorporated in formulations, such as hard- and soft-gelating capsules, and normal and gastro-resistant tablets. In nutritional preparations for humans for the prevention of atherosclerosis or for the prevention of tumors, lycopene can advantageously be combined with procyanidole polyphenols such as those prepared from *Vitis vinifera* and *Camellia sinensis*. When lycopene is used in a substantially pure form, for the preparation of bio-available formulations, the addition of phospholipids as stabilizers and emulsifiers is convenient. In the unpurified extracts, phospholipids are already present as they are added during the extraction process.

EXAMPLES

The following examples further illustrate the invention. The invention is not limited, however, to the specific embodiments disclosed in the following examples.

Example I

Preparation of a lycopene-enriched lipophilic extract from *Lycopersicum esculentum*

10 kg of mature tomatoes (*Lycopersicum esculentum* var. *Sanmarzano*) are homogenized in a knife mill to a semi-fluid mass; the fluid slurry is heated for about three hours with flowing steam to 95° C. and maintained under these temperature conditions with slow stirring for about 30 minutes. During heating, a red flocculate separates consisting of denatured vegetable cell structures which tend to precipitate immediately. This suspension is cooled at 60° C. and centrifuged; the supernatant which does not contain lycopene is discarded and the residue is washed in a centrifuge with water thereby removing any undesired substances. The biomass still containing about 50% of water is extracted for 3 hours with strong stirring and under mild reflux with 2.5 l of n-hexane containing 0.01% soy lecithin. After separation of the solvent, the residue is re-extracted with a further 2 l of n-hexane under the same conditions as used in the first extraction. The extraction solvent after filtration and complete decantation is concentrated under vacuum until the solvent is removed completely. 11 g of a bright red-coloured oily residue containing 0.52 g of lycopene are obtained. This extract can be used as such in the formulations for use in humans.

Example II

Preparation of a lycopene-enriched lipophilic extract starting from dried skins of *Lycopersicum esculentum*

10 kg of mature tomatoes (*Lycopersicum esculentum* var. *Sanmarzano*) are coarsely ground and filtered by squeezing through a grid which allows the separation of the fruit skins and seeds. The resultant residue is quickly dehydrated in an air stream. About 150 g of a brightly coloured material are obtained, which is separated from the seeds and finely ground. The ground residue is treated in a mixer with 150 ml of water and left to stand for about one hour, thereby allowing the vegetable material to swell, resulting in the breaking of the cells due to membrane porosity. This wet mass is extracted with 800 ml of n-hexane containing 0.01% soy lecithin with stirring under mild reflux. After 3 hours the solvent is removed and the vegetable residue is extracted again twice with 400 ml each of n-hexane. The combined extracts are filtered, decanted, then concentrated under vacuum until the solvent is completely removed. 5.2 g of a bright red-coloured oily residue containing 4.6% of lycopene are obtained. This extract can be used as such in the formulation for use in humans.

Example III

Preparation of a lycopene-enriched lipophilic extract starting from not-dried skins of *Lycopersicum esculentum*

The industrial squeezing residue of fresh tomatoes, obtained under conditions similar to those reported in example II, is separated from the juice, washed with water, pressed to remove the residual water as much as possible and frozen. For the extraction, the frozen mass is ground at a temperature of −20° C. and then extracted according to the procedure of example II. 250 g of a frozen biomass yield 4.2 g of a bright red-coloured oily residue containing 5.6% of lycopene. This extract can be used as such in the formulations for use in humans.

Example IV

Preparation of pure lycopene by extraction from the enriched lipophilic extract 0.5 kg of lycopene oil, prepared according to example I, are extracted in counter-current with carbon dioxide in supercritical conditions, using a three step column working at different temperatures (50, 40, 34° C.) and under a 180 bars pressure. In these conditions, the purification of the extract is achieved and lycopene is recovered by crystallization of the residue which has not been distilled during the fractionation. 24 g of a pure product are obtained, having the same chemical-physical and spectroscopical characteristics as lycopene.

Example V

Preparation of coated tablets containing the lycopene-enriched lipophilic extract

| | | |
|---|---|---|
| Lycopene-enriched lipophilic extract | 10.00 | mg |
| Lactose | 50.60 | mg |
| Pre-gelatinized starch | 73.60 | mg |
| Microcrystalline cellulose | 49.80 | mg |
| Cross-linked sodium carboxymethylcellulose | 19.00 | mg |
| Colloidal silica | 19.00 | mg |
| Hydroxypropyl cellulose | 5.00 | mg |
| Hydrogenated vegetable oils | 2.00 | mg |
| Soy lecithin | 1.00 | mg |
| Hydroxypropyl methylcellulose | 6.07 | mg |
| Talc | 3.96 | mg |
| Triacetin | 1.21 | mg |
| Titanium dioxide | 0.40 | mg |
| Red iron oxide | 0.24 | mg |
| Polyethylene glycol 6000 | 0.12 | mg |

Example VI

Preparation of hard-gelatin capsules containing the lycopene-enriched lipophilic extract

| | | |
|---|---|---|
| Lycopene-enriched lipophilic extract | 10.00 | mg |
| Lactose | 50.60 | mg |
| Pre-gelatinized starch | 73.60 | mg |
| Microcrystalline cellulose | 49.80 | mg |
| Cross-linked sodium carboxymethylcellulose | 19.00 | mg |
| Colloidal silica | 19.00 | mg |
| Hydroxypropyl cellulose | 5.00 | mg |
| Hydrogenated vegetable oils | 2.00 | mg |
| Soy lecithin | 1.00 | mg |

Example VII
Preparation of hard-gelatin capsules containing lycopene

| | |
|---|---|
| Lycopene | 5.00 mg |
| Lactose | 40.00 mg |
| Pre-gelatinzed starch | 53.00 mg |
| Microcrystalline cellulose | 30.00 mg |
| Colloidal silica | 5.00 mg |
| Hydrogenated vegetable oils | 2.00 mg |
| Cross-linked sodium carboxymethylcellulose | 19.00 mg |
| Hydroxypropyl cellulose | 5.00 mg |

Example VIII
Preparation of soft-gelating capsules containing the lycopene-enriched lipophilic extract

| | |
|---|---|
| Lycopene-enriched lipophilic extract | 10.00 mg |
| Peanut oil | 151.00 mg |
| Partially hydrogenated vegetable oils | 80.00 mg |
| Soy lecithin | 1.00 mg |
| Coating | |
| Gelatin | 82.00 mg |
| Glycerol | 40.10 mg |
| Glycine | 1.87 mg |
| Red iron oxide | 1.42 mg |

We claim:

1. A process of extracting lycopene from *Lycopersicum esculentum* which comprises combining a quantity of *Lycopersicum esculentum* containing lycopene with a sufficient amount of an extraction medium comprising at least one solvent selected from the group consisting of aromatic hydrocarbons, aliphatic hydrocarbons, and halohydrocarbons and from about 0.01 to about 0.100 w/v of the extraction medium of a surfactant and stabilizing agent comprising a phospholipid to extract at least a portion of said lycopene from said *Lycopersicum esculentum*.

2. The process of claim 1 wherein said solvent is selected from the group consisting of n-hexane and methylene chloride.

3. The process of claim 2 wherein n-hexane is selected as the solvent.

4. The process of claim 1 which further comprises selecting soy lecithin as said phospholipid.

5. The process of claim 1 which further comprises forming a slurry by at least partially homogenizing said *Lycopersicum esculentum* prior to adding said extraction medium.

6. The process of claim 5 wherein said *Lycopersicum esculentum* is at least partially dried and wherein said method further comprising adding to said slurry about one-half part by weight of water to lyse the cells of the *Lycopersicum esculentum*.

7. The process of claim 5 which further comprises heating said slurry to a temperature of from about 70–100° C. prior to adding said extraction medium.

8. The process of claim 7 wherein said slurry is heated for between about 15–60 minutes.

9. The process of claim 7 which further comprises cooling said heated slurry at a temperature of between about 50–70° C. prior to addition of said extraction medium.

10. The process of claim 9 wherein said cooling is carried out under substantially sterile conditions.

11. The process of claim 1 which further comprises concentrating said extract by removing at least a portion of the extraction medium therefrom.

12. The process of claim 11 which comprises removing a sufficient quantity of said extraction medium from the extract to concentrate the lycopene to an amount of from about 1 to about 10% by weight.

13. The process of claim 1 wherein the lycopene extract is further purified by chromatographic separation through an acidic alumina column wherein the lycopene is eluted with a mixture of ethyl acetate and hexane.

14. The process of claim 1 wherein the lycopene extract is further purified by extraction with $CO_2$ at a temperature of between about 35–65° C. and a pressure of between about 150–200 bars.

15. The process of claim 1 which further comprises adding a predetermined amount of said lycopene to a composition suitable for use as a food or a cosmetic.

16. A process for extracting lycopene from *Lycopersicum esculentum* which comprises:

forming a slurry by at least partially homogenizing a quantity of Lycopersicum esculentum containing lycopene;

heating said slurry to a temperature of from about 70 to about 100° C. for a time of from about 15 to about 60 minutes;

cooling said heated slurry to a temperature of from about 50 to about 70° C.; and adding to said cooled slurry a sufficient amount of an extraction medium comprising at least one solvent selected from the group connecting of aromatic hydrocarbons, aliphatic hydrocarbons and halohydrocarbons and from about 0.01 to about 0.100 w/v of the extraction medium of a surfactant and stabilizing agent comprising a phospholipid to extract at least a portion of said lycopene from said *Lycopersicum esculentum*.

17. The process of claim 16 wherein said solvent is selected from the group consisting of n-hexane and methylene chloride.

18. The process of claim 16 which further comprises selecting soy lecithin as said phospholipid.

19. The process of claim 16 which further comprises removing a sufficient quantity of said extraction medium from the extract to concentrate the lycopene to an amount of from about 1 to about 10% by weight.

20. The process of claim 16 wherein the lycopene extract is further purified by chromatographic separation through an acidic alumina column wherein the lycopene is eluted with a mixture of ethyl acetate and hexane.

21. The process of claim 16 wherein the lycopene extract is further purified by extraction with $CO_2$ at a temperature of between about 35–65° C. and a pressure of between about 150–200 bars.

22. The process of claim 16 which further comprises adding a predetermined amount of said lycopene to a composition suitable for use as a food or a cosmetic.

* * * * *